US00PP13131P2

(12) United States Plant Patent
Zaiger et al.

(10) Patent No.: US PP13,131 P2
(45) Date of Patent: Oct. 29, 2002

(54) CHERRY TREE NAMED 'ROYAL DAWN'

(76) Inventors: Chris Floyd Zaiger, 929 Grimes Ave., Modesto, CA (US) 95358; Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 131 days.

(21) Appl. No.: 09/758,507

(22) Filed: Jan. 12, 2001

(65) Prior Publication Data

US 2002/0095698 P1 Jul. 18, 2002

(51) Int. Cl.[7] ..... A01H 5/00
(52) U.S. Cl. ..... Plt./181
(58) Field of Search ..... Plt./181

*Primary Examiner*—Bruce R. Campell
*Assistant Examiner*—Annette H. Para

(57) ABSTRACT

A new and distinct variety of cherry tree (*Prunus avium*). Its novelty consists of the following unique combination of desirable features that are outstanding in a new variety. The following features of the tree and its fruit are characterized with the tree budded on Mahaleb rootstock (non-patented), grown on Hanford sandy loam soil with Storie Index rating 95, in USDA Hardiness Zone 9, near Modesto, Calif., and with standard commercial cultural fruit growing practices, such as pruning, thinning, spraying, irrigation and fertilization.

1. Heavy and regular production of medium to large size fruit.
2. Fruit with an attractive red skin color.
3. The ability of the fruit to hold firm on the tree 12 to 14 days after maturity (shipping ripe).
4. Fruit with firm flesh, good handling and shipping quality.
5. Vigorous, upright tree growth.
6. Fruit with excellent flavor and eating quality.

1 Drawing Sheet

BOTANICAL CLASSIFICATION

*Prunus avium* cultivar Royal Dawn.

BACKGROUND OF THE VARIETY

In the field of plant genetics we conduct an extensive and continuing plant-breeding program including the origination and sexual reproduction of orchard trees, and of which interspecifics, plums, peaches, nectarines, apricots and cherries are exemplary. It is against this background of our activities that the present variety of cherry tree was originated and asexually reproduced by us in our experimental orchard located near Modesto, Stanislaus County, Calif.

PRIOR VARIETIES

The existing variety of cherry tree which is known to use, and mentioned herein, Bing Cherry (non-patented).

ORIGIN OF THE VARIETY

The present new variety of cherry tree (*Prunus avium*) was developed by us in our experimental orchard located near Modesto, Calif. It was selected in 1984 from a group of open pollinated seedlings grown from the seed of a seedling with the field identification number 32G500 (non-patented). The seedling 32G500 was selected by us to be used in our breeding program and originated from a group of open pollinated seed of unknown parentage. We grew a large number of open pollinated seedlings on their own root and under close and careful observation, one such seedling, which is the present variety, having heavy production with excellent fruit quality was selected for asexual propagation and commercialization.

ASEXUAL REPRODUCTION OF THE VARIETY

Asexual reproduction of the new and distinct variety of cherry tree was by budding to Mahaleb rootstock (non-patented), a standard rootstock for cherried in California, as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

The new and distinct variety of cherry tree is of large size, vigorous, upright growth and a regular bearer of medium to large, firm fruit with excellent flavor and eating quality. The fruit is further characterized for its good handling and shipping quality, its ability to hold firm on the tree 12 to 14 days after maturity (shipping ripe) and having an attractive red skin color. In comparison to the popular standard commercial cherry variety Bing (non-patented), the new variety blooms 5 to 6 days earlier and the fruit is 10 to 11 days earlier in maturity.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is possible in a color representation of this type.

DESCRIPTION OF THE VARIETY

The following is a detailed botanical description of the new variety of cherry tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Tree height prune to 12 to 14 feet in height for economical harvesting of fruit.

*Vigor.*—Vigorous. Tree growth reaching 5 to 7 feet in height the first growing season. Growth rate varies with soil type and depth, cultural practices and climatic conditions.

*Productivity.*—Precocious and very productive of medium to large size fruit.

*Bearer.*—Regular, adequate fruit set for 10 consecutive years.

*Form.*—Upright. During the first and second growing season scaffolds are selected and tied down to increase crotch angle and help spread tree to desired width of 12 to 14 feet.

*Density.*—Medium dense, pruning and removal of center branches and leaves to form open vase shape for added sunlight and air movement to center of tree to enhance health of fruit spurs, fruit color and more uniform brix throughout the tree.

*Hardiness.*—Tree grown in USDA Hardiness Zone 9. Winter chilling requirement is approximately 750 hours at or below 45° F.

Trunk:

*Size.*—Large. Measured 34 inches in circumference at 22 inches above ground on 14 year old tree. Varies with soil type, climatic conditions and cultural practices.

*Texture.*—Medium rough, increases slightly with age of tree.

*Color.*—Soot brown to dark brown (5-E-3) to (5-F-6).

Branches:

*Size.*—Medium. Average circumference of 10 inches measured 50 inches above ground.

*Surface.*—Smooth to medium rough, varies with age of growth.

*Color.*—New growth (first year wood) greenish tan to light tan (3-D-5) to (5-D-6). Older growth varies from light brown to brown (6-E-5) to (6-F-4).

*Lenticels.*—Medium size. Medium number, average 11 in a 4 square inch section. Varies from 1/8 inch to 1/4 inch in length and 1/32 inch to 3/32 inch in width. Size increases as branch increases in size. Color — brownish yellow to light brown (5-C-8) to (5-D-8).

Leaves:

*Size.*—Large. Average length 6 3/4 inches. Average width 2 1/2 inches.

*Form.*—Oblanceolate, pointed.

*Margin.*—Double serrate.

*Thickness.*—Medium.

*Surface.*—Smooth.

*Petiole.*—Average length 1 3/8 inches. Average width 3/32 inch. Grooved longitudinally.

*Glands.*—Reniform. Large size. Average diameter 1/8 inch. Number varies from 1 to 4, average 2. Color varies from grayish orange to grayish red (6-B-4) to (7-B-4). Located primarily on upper portion of petiole.

*Color.*—Upper surface — green to dark green (28-F-4) to (28-F-8). Lower surface — jade green to green (28-E-5) to (28-E-7).

Flower buds:

*Number per spur.*—Average number 6, varies from 1 to 7.

*Size.*—Small to medium. Average length 7/8 inch. Average width 1/2 inch.

*Form.*—Conical, plump.

Flowers:

*Number per flower bud.*—Average number 4, varies from 3 to 5.

*Size.*—Large. Average height 9/16 inch. Average diameter 1 1/3 inches.

*Petal.*—Obovate. Average length — 39/64 inch. Average width — 17/32 inch. Outer edge slightly scalloped.

*Pistil.*—Number per flower — usually one. Average length 7/16 inch. Color — whitish to pale yellow (4-A-2) to (4-A-3).

*Stamens.*—Number per flower — 25 to 30. Filament length — 9/25 inch. Filament color — white (1-A-1). Anther color — light yellow to maize yellow (4-A-5) to (4-A-7).

*Pollen.*—Present, pollenizer required — not self fruitful.

*Pedicel.*—Medium length. Color — light green to olive green (2-D-4) to (2-D-5).

*Aroma.*—Wanting.

*Blooming period.*—Date of First Bloom: Mar. 18, 1998. Date of Last Bloom: Mar, 28, 1998. Varies slightly with climatic conditions.

*Color.*—White (1-A-1).

Fruit:

*Maturity when described.*—Firm (shipping ripe).

*Date of first picking.*—May 11, 1998.

*Date of last picking.*—May 18, 1998. Varies slightly with climatic conditions.

*Size.*—Average diameter axially — 15/16 inch to 1 inch. Average transversely in suture plane — 15/16 inch to 1 inch. Average weight — 10.6 grams. Average weight varies slightly with amount of fruit set, soil type and fertility, cultural practices and climatic conditions.

*Form.*—Globose, slightly flattened at apex and base.

*Suture.*—Varies from slightly lipped to nearly smooth, extends from base to apex.

*Ventral surface.*—Nearly smooth, some fruit slightly grooved near base.

*Apex.*—Varies from slightly retuse to rounded.

*Base.*—Retuse.

*Cavity.*—Rounded to slightly elongated in suture plane. Average depth — 1/16 inch. Average breadth — 1/8 inch.

Flesh:

*Ripens.*—Evenly.

*Texture.*—Firm, meaty.

*Fibers.*—Few, small, tender, cream color.

*Aroma.*—Very slight.

*Eating quality.*—Excellent.

*Flavor.*—Excellent, sweet, good balance between sugar and acid.

*Juice.*—Moderate, enhances flavor.

*Brix.*—19.7°, varies slightly with amount of crop load and climatic conditions.

*Color.*—Cardinal red to maroon (10-F-8) to (11-E-8). Pit cavity — dark ruby (11-F-5) to (12-F-5).

Skin:

*Thickness.*—Medium, tenacious to flesh.

*Texture.*—Medium.

*Down.*—Wanting.

*Tendency to crack.*—None during dry weather, only slight tendency to crack in wet weather, varies with stage of fruit maturity.

*Color.*—Garnet red to dark ruby (11-E-8) to (11-F-5).

Stem:

*Size.*—Length varies from 1 inch to 1⅜ inches. Average width 1/16 inch.

*Color.*—Varies from grayish green to olive green (30-C-8) to (30-D-8).

Stone:

*Type.*—Semi-clingstone.

*Size.*—Small. Average length — 13/32 inch. Average width — 11/32 inch. Average thickness — 9/32 inch.

*Form.*—Slightly elongated.

*Base.*—Nearly rounded, extending slightly longer at suture attachment.

*Apex.*—Rounded.

*Surface.*—Smooth, except for ridges near suture.

*Sides.*—Equal.

*Ridges.*—A small, narrow ridge on each side of suture, extending from base to apex.

*Tendency to split.*—None.

*Color.*—Varies from sand to light tan when dry (3-B-4) to (4-B-4).

Use: Market. Local and long distance.

Keeping quality: Good, held well for 2 weeks in cold storage at 38 to 42° F. and maintained good firmness and eating quality.

Shipping quality: Good, no excessive bruising or scarring in packing and shipping trials.

Disease resistance/susceptibiity: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of cherry tree, substantially as illustrated and described, characterized by its large size, vigorous, upright growth and being a heavy and regular bearer of medium to large, firm, fruit with excellent flavor and eating quality; the fruit is further characterized by holding firm on the tree for 12 to 14 days after maturity (shipping ripe), having good handling and shipping quality and, in comparison to the Bing Cherry (non-patented), the new variety blooms 5 to 6 days earlier and the fruit is approximately 10 to 11 days earlier in maturity.

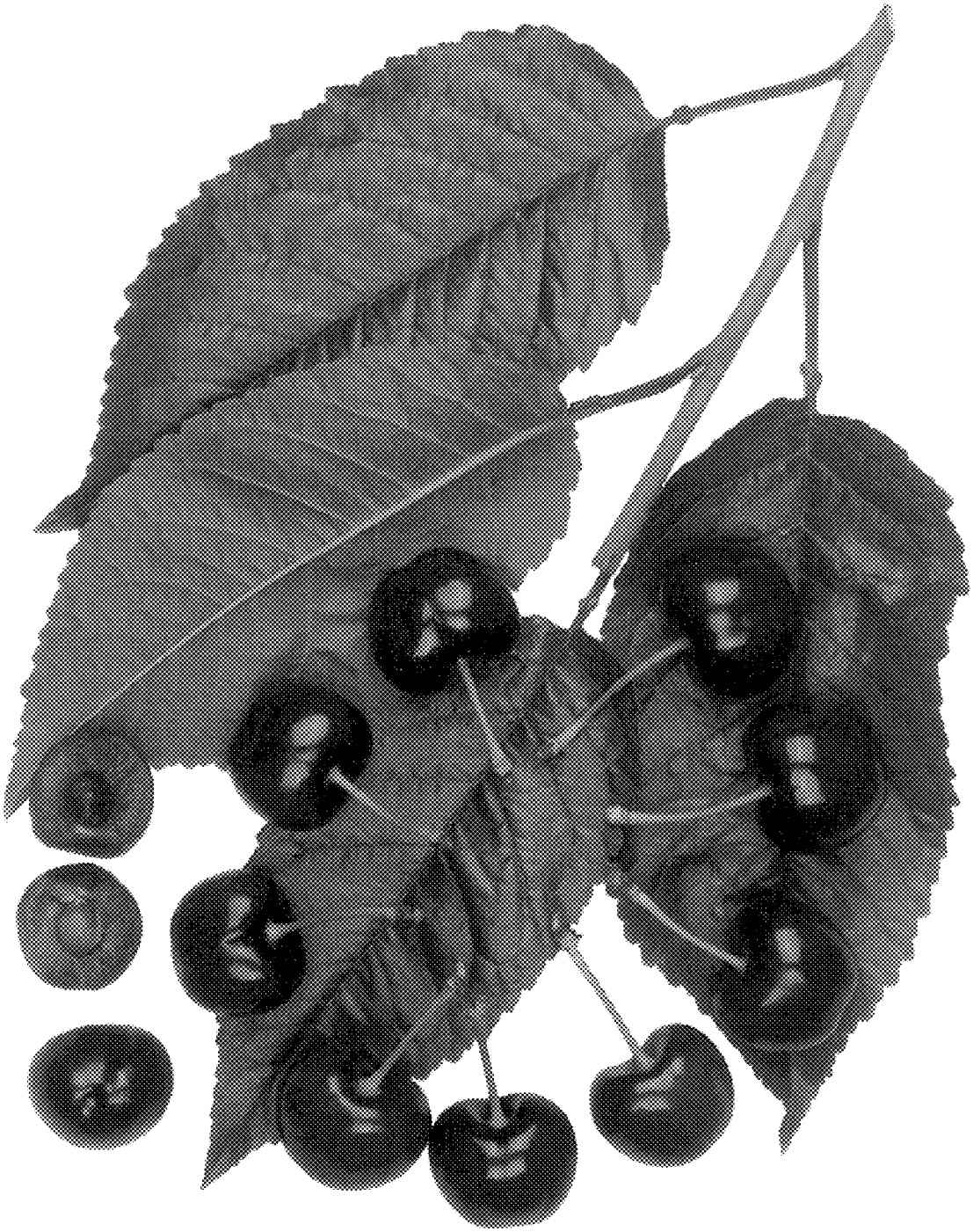

* * * * *